United States Patent
Sift Carter (10) Patent No.: US 9,907,782 B2
(45) Date of Patent: Mar. 6, 2018

(54) TREATMENT OR PREVENTION OF SEBORRHEIC KERATOSIS USING ARTEMISININ AND DERIVATIVES THEREOF

(71) Applicant: EPIPHARM AG, Binningen (CH)

(72) Inventor: Rosemarie Sift Carter, Basel (CH)

(73) Assignee: EPIPHARM AG, Binningen (CH)

( * ) Notice: Subject to any disclaimer, the term of this patent is extended or adjusted under 35 U.S.C. 154(b) by 0 days.

(21) Appl. No.: 15/305,516

(22) PCT Filed: Apr. 27, 2015

(86) PCT No.: PCT/EP2015/059104
§ 371 (c)(1),
(2) Date: Oct. 20, 2016

(87) PCT Pub. No.: WO2015/165856
PCT Pub. Date: Nov. 5, 2015

(65) Prior Publication Data
US 2017/0035727 A1    Feb. 9, 2017

(30) Foreign Application Priority Data

Apr. 28, 2014   (EP) .................................. 14166277

(51) Int. Cl.
| | |
|---|---|
| A61K 31/357 | (2006.01) |
| A61K 9/00 | (2006.01) |
| A61K 9/06 | (2006.01) |
| A61K 45/06 | (2006.01) |
| A61K 31/192 | (2006.01) |
| A61K 31/196 | (2006.01) |
| A61K 31/366 | (2006.01) |
| A61K 31/381 | (2006.01) |
| A61K 31/405 | (2006.01) |
| A61K 31/5415 | (2006.01) |
| A61K 31/542 | (2006.01) |
| A61K 31/573 | (2006.01) |
| A61K 31/60 | (2006.01) |
| A61K 31/616 | (2006.01) |
| A61M 37/00 | (2006.01) |

(52) U.S. Cl.
CPC .......... *A61K 31/357* (2013.01); *A61K 9/0014* (2013.01); *A61K 9/06* (2013.01); *A61K 31/192* (2013.01); *A61K 31/196* (2013.01); *A61K 31/366* (2013.01); *A61K 31/381* (2013.01); *A61K 31/405* (2013.01); *A61K 31/542* (2013.01); *A61K 31/5415* (2013.01); *A61K 31/573* (2013.01); *A61K 31/60* (2013.01); *A61K 31/616* (2013.01); *A61K 45/06* (2013.01); *A61M 37/00* (2013.01); *A61M 2037/0007* (2013.01)

(58) Field of Classification Search
None
See application file for complete search history.

(56) References Cited

U.S. PATENT DOCUMENTS

| | | |
|---|---|---|
| 4,196,204 A | 4/1980 | Petzoldt et al. |
| 4,978,676 A | 12/1990 | Thornfeldt |
| 7,381,427 B2 | 6/2008 | Ancira |
| 8,013,011 B2 | 9/2011 | Sift Carter |
| 8,193,376 B2 | 6/2012 | Gupta |
| 9,402,823 B2 | 8/2016 | Zibert et al. |
| 2008/0255223 A1 | 10/2008 | Sift Carter |
| 2010/0061948 A1 | 3/2010 | Park et al. |
| 2011/0077193 A1 | 3/2011 | Gupta |
| 2013/0259815 A1 | 10/2013 | Loy et al. |
| 2013/0338226 A1 | 12/2013 | Zibert et al. |

FOREIGN PATENT DOCUMENTS

| | | |
|---|---|---|
| EP | 0428773 A1 | 5/1991 |
| JP | H03170422 A | 7/1991 |
| KR | 20120085953 A | 8/2012 |
| WO | 2007045116 A1 | 4/2007 |
| WO | 2012080466 A2 | 6/2012 |

OTHER PUBLICATIONS

C. G. Burkhart et al.,"Use of a Keratolytic Agent With Occlusion for Topical Treatment of Hyperkeratotic Seborrheic Keratoses", Skinmed. 2008; 7, pp. 15-18.
D. Gill et al., "The Prevalence of Seborrheic Keratoses in People Aged 15 to 30 Years", Arch Dermatol. vol. 36, 2000, pp. 759-762.
M. D. Herron et al., "Seborrheic keratoses: A study comparing the standard cryosurgery with topical calcipotriene, topical tazarotene, and topical imiquimod", International Journal of Dermatology 2004, 43, pp. 300-302.

*Primary Examiner* — Kortney L Klinkel
*Assistant Examiner* — Tori M Strong
(74) *Attorney, Agent, or Firm* — Abel Law Group, LLP (57) ABSTRACT

The invention relates to a method of treating or preventing seborrheic keratosis. The method comprises locally applying to a subject in need thereof artemisinin and/or one or more structurally related compounds. Also disclosed are topical formulations comprising artemisinin and/or one or more structurally related compounds.

20 Claims, 1 Drawing Sheet

TREATMENT OR PREVENTION OF SEBORRHEIC KERATOSIS USING ARTEMISININ AND DERIVATIVES THEREOF

BACKGROUND

The present invention relates to the treatment or prevention of seborrheic keratosis of the skin with locally applied formulations; in particular topical formulations. Furthermore, it relates to topical formulations suitable for this purpose.

Seborrheic keratosis is one of the most common non-cancerous, benign, epidermal skin tumors. It is a harmless skin growth that originates in keratinocytes of the epidermis. Keratinocytes are the predominant cell type in the epidermis, the outermost layer of the skin, constituting 80% of the cells found there. Those keratinocytes found in the basal layer (stratum basale) of the epidermis are sometimes referred to as "basal cells" or "basal keratinocytes".

The primary function of keratinocytes is the formation of a barrier against environmental damage such as pathogens (bacteria, fungi, parasites, and viruses), heat, UV radiation and water loss. Keratinization is part of the physical barrier formation (cornification), in which the keratinocytes produce more and more keratin and undergo terminal differentiation. The fully cornified keratinocytes (corneocytes) that form the outermost layer, the stratum corneum, are constantly shed off and replaced by new corneocytes.

Within the epidermis, keratinocytes are associated with other cell types such as melanocytes and Langerhans cells. Keratinocytes modulate the immune system and are potent producers of anti-inflammatory mediators (such as IL-10 and TGF-β). Keratinocytes also contribute to protecting the body from ultraviolet radiation by modulating the skin pigmentation, taking up and storing melanosomes, vesicles containing the endogenous photoprotectant melanin, from epidermal melanocytes.

Seborrheic keratosis occurs in form of so-called growths, or lesions, (which are also referred to as seborrheic keratoses), which may be found in many areas of the body, including the face, ears, neck, arms, chest, shoulders, back and stomach as well as the back of the hands. Unlike warts, though, they are usually not found on the soles of the feet or the palms.

The lesions may be round or oval in shape and feel either slightly elevated (e.g. like scab on a healing wound) or completely flat. The formation of the lesions typically involves hyperkeratosis and acanthosis (a diffuse epidermal hyperplasia; i.e. a thickening of the epidermis by increased proliferation of cells in the stratum basale and stratum spinosum). They often start as small flat, rough areas, and over time develop a thicker, exophytic, sometimes fissured, wart-like surface, which may have a waxy, greasy, sebaceous appearance; thus the term "seborrheic". Sometimes, pseudo-cystic inversions and inclusion of horn-globules may be seen in/on the lesion. Mostly, the lesions look as if they were pasted onto the skin, because they have well-defined demarcation lines to the surrounding skin and typically only the top layers of the epidermis, i.e. the outermost layer of our skin, are involved in their formation. The size of the lesions ranges from very small ones of only a few millimeters up to more than 2.5 centimeters.

The lesions may have various colors, ranging from white or yellow, light tan to dark brown, sometimes black, depending on the extent of melanin content. Rarely, they may also be white or yellow. Although seborrheic keratoses are often associated with increased pigmentation and may resemble moles, nevi, liver spots or lentigos, they have to be distinguished from such melanocytic hyperpigmented tumors/lesions which are caused by a dysfunction of melanocytes. Unlike e.g. nevi (which are based on an abnormal proliferation of melanocytes located on the basal layer of epidermis, the junctional zone between epidermis and dermis), seborrheic keratosis originates in the keratinocytes as mentioned above.

In some cases, seborrheic keratosis lesions may further be difficult to distinguish from melanoma, a very serious type of skin cancer, which is why they should be checked by a dermatologist in case of doubt.

Seborrheic keratoses are also known as "seborrheic verruca", "or "seborrheic warts, "senile warts", "benign acanthokeratosis" and as "basal cell papilloma". However, these terms used for seborrheic keratosis are misleading. Firstly, seborrheic keratosis is not limited to a seborrheic distribution (scalp, mid-face, chest, upper back), nor are they formed from sebaceous glands as is the case with sebaceous hyperplasia. Secondly, seborrheic keratosis has nothing in common with warts (verruca), they are not of viral origin and are not associated with the human papilloma virus. The term "senile wart" is also a misnomer. Although the onset is usually in middle age (over 40) they are a common finding also in younger patients; e.g. 12% of the 15-25 year-olds (Gill D., Dorevitch A., Marks R.; The prevalence of seborrheic keratoses in people aged 15 to 30 years: is the term senile keratosis redundant? Arch. Dermatol. 2000 June; 136(6):759-62).

Variants of seborrheic keratoses include Stucco keratoses: numerous small dry grey stuck-on lesions usually found on lower legs and feet; Dermatosis papulosa nigra: numerous brown, warty papules on face, neck and chest of dark-skinned individuals; Irritated seborrheic keratoses: inflamed lesions, often red and crusted which may resemble a skin cancer; and Lichenoid keratosis: resolving keratosis or lentigo, often pink or grey-colored.

The cause of seborrheic keratosis, or the exact mechanism of the formation of seborrheic keratosis lesions, is not known. Seborrheic keratoses are considered degenerative in nature, appearing as part of the skin aging process. As time goes by, seborrheic keratoses become more numerous. Men and women are affected alike. Some people inherit a tendency to develop a very large number of them.

The majority of lesions appear on skin areas which are usually covered by clothes, such as chest, shoulders, back and stomach; thus UV-light exposure does not seem to be the cause of seborrheic keratosis lesions. Other external factors, physical and/or chemical, do not seem to foster seborrheic keratosis.

And neither the presence nor absence of any specific protein is unique to seborrheic keratosis. The lesions are believed to consist of accumulated senescent epidermal cells in G1-phase arrest of the cell cycle that histologically fail to differentiate like normal epidermal basal cells, although they do multiply, keratinize, and mature into squamous cells. Immuno-histochemical analyses have shown differences between lesion cells and normal skin cells in cytokeratins, involucrin, ras p21, and epidermal transglutaminase expression. Seborrheic keratosis cells were further found to have increased expression of interleukin-2, tumor necrosis factor-a, endothelin-converting enzyme-1 α, p73, interferon-γ, and lymphotoxin mRNA and down-regulation of IL-1 α compared with peri-lesional normal epidermis.

The fact that seborrheic keratosis often runs in families, with the risk increasing with the number of affected relatives, suggests a certain genetic disposition. Newer studies, for example, indicate a frequent activating mutation of the FGF-receptor (fibroblast growth factor) as a possible mechanism. Others propose a cyclin-dependent kinase inhibitor, p16, that is expressed in all lesion cells, or an imbalance in the p53 and Bcl-2 proteins; all leading to suppression of apoptosis, and hence accumulation of cells (Burkhart et al.; "Use of a keratolytic agent with occlusion for topical treatment of hyperkeratotic seborrheic keratoses"; SKINmed: Dermatology for the Clinician, Vol. 7, Issue 1, p. 15-18, January/February 2008).

Seborrheic keratosis lesions are benign, non-contagious and—unlike e.g. nevi—do not develop to (pre)-cancerous stages. Only very rarely, eruptive seborrheic keratoses may denote an underlying internal malignancy, e.g. gastrointestinal adenocarcinoma. The syndrome is known as the sign of Leser-Trélat. A dermatologist may decide to remove one or more lesions for differential diagnosis purposes if they have a suspicious appearance, or simply if they are causing physical or emotional discomfort to the patient; e.g. if the lesions are considered unsightly and/or if lesions interfere with clothes, jewelry, razors during shaving or the like, which may lead to bleedings and infections. This physical or emotional discomfort of the patient is often so intense and long-lasting, that the patients express a strong desire to get rid of the lesions or to at least reduce their size and/or coloration.

Commonly used removal methods include cryo-therapy, electro-therapy, curettage and laser treatment (e.g. using erbium-YAG-lasers). During cryo-therapy the lesions are sprayed or swabbed with liquid nitrogen which causes them to freeze, form minor blisters and flake off during the subsequent days or weeks. With electro-therapy the lesions are treated with an electrical current causing them to desiccate and/or evaporate. Electro-therapy may be combined with curettage, which means scraping the lesions off using a sharp spoon or a sling; the latter may apply an electrical current on the lesion while scraping it off to prevent bleeding. This is also called cauterization. Typically the area is numbed before the procedure. Nonetheless, the methods are invasive, painful and associated with certain risks such as scarring and skin discoloration.

Some online shops offer herbal pills for oral ingestion to target seborrheic keratosis, such as Kenofax, Rhinical, Sebeton or Sebarec. These pills contain a wide range of plant extracts from e.g. Swertia Chirata, Fumaria Officinalis, Tephrosa Purpurea, Sphaeranthus Indicus, Zizyphus Vulgaris, Terminalia Chebula, Cassia Absus, Melia Azadirachta, Lycopodium Clavatum, Berberis Aristata. While presumably common in the Himalayans, the majority of these plants are not considered approved and well-known medicinal plants throughout Europe or North-America. Thus, apart from the apparent lack of toxicity studies for these pills and the potentially doubt-worthy manufacturing methods- and sites, there remains the risk of allergic reactions to one or more of the multicomponent mixtures in said pills. Furthermore, they do not provide for a topical or local treatment which is preferred by many in order to limit undesirable side effects.

Some topical formulations applied in the (cosmetic) treatment of e.g. skin discolorations and/or skin diseases associated with hyperkeratosis have been disclosed in the prior art.

For instance, WO 2012/080466 describes ingenol compounds, such as ingenol-3-angelate, and their topical use in treating seborrheic keratosis. The ingenol compounds are e.g. administered in the form of an isopropyl alcohol-based gel.

Herron et al. tested topical formulations of typical psoriasis drugs on seborrheic keratosis lesions in daily or bi-daily application regimens: calcipotriene (0.005% ointment), tazarotene (0.1% cream) or imiquimod (5% cream) ("Seborrheic keratoses: A study comparing the standard cryosurgery with topical calcipotriene, topical tazarotene, and topical imiquimod"; Int. J. Dermat.; Vol. 43, Issue 4, pages 300-302, April 2004). Herron et al. tried to benefit from calcipotriene's and tazarotene's promoting effects on keratinocyte differentiation and their antiproliferative effects, as well as imiquimod's immune modulatory effect which was successful with refractory warts and molluscum contagiosum, and neoplasms such as pre-malignant keratosis and squamous cell carcinoma. The results were not satisfactory: once daily application of calcipotriene, tazarotene and imiquimod did not result in any clinical improvement. And bi-daily application of tazarotene caused clinical and histological improvement in less than half the patients only. In addition, effectiveness of tazarotene was limited by its irritation, with ⅔ of the patients reporting burning, pruritus and redness. Furthermore, tazarotene, as most retinoids, is not allowed during pregnancy and women of childbearing potential would have to use adequate birth control measures when using tazarotene topically.

U.S. Pat. No. 7,381,427 B2 discloses topical compositions and methods for the treatment, removal, elimination and prevention of seborrheic keratoses utilizing safe, dependable, effective, biocompatible treatments with no scarring, bleeding, burning, freezing, shocking, and hypopigmentation or hyperpigmentation; said treatments involving the use of high concentration hydrogen peroxide as the active agent (at least about 23%; e.g. 43-48%). Optionally, the compositions may further contain vitamins, amino acids, melanin inhibitors such as kojic acid, organic acids such as lactic acid, and hormones such as melatonin and/or various other components. It is noted that U.S. Pat. No. 7,381,427 B2 is silent on artemisinin or its derivatives or similar plant extracts from the same family. Additionally, more than once the authors mention seborrheic keratoses that have become malignant or are at risk of becoming malignant, which according to common knowledge on seborrheic keratosis does not occur with these types of lesions. This may indicate that the authors give the term seborrheic keratosis a much broader meaning than has been established in the scientific community, e.g. also covering other skin-conditions such as nevi which have a different etiopathogenesis from seborrheic keratoses as commonly defined.

Burkhart et al. reported in 2008 that still no topical treatment was commonly recommended for seborrheic keratosis lesions and thus tested 50% urea under occlusion in order to treat unsightly lesions ("Use of a keratolytic agent with occlusion for topical treatment of hyperkeratotic seborrheic keratoses"; SKINmed: Dermatology for the Clinician, Volume 7, Issue 1, pages 15-18, January/February 2008). Keratolytic substances such as urea, salicylic acid, lactic acid and retinoic acid are known to the skilled person since a long time and have been applied in form of e.g. creams, ointments, pastes, solutions and lacquers; e.g. in order to soften the skin's keratin and thereby treat warts and other lesions in which the epidermis produces excess skin. While no side effects were reported, the success of applying urea and digitally scraping the lesions was limited: some reduction of the thickness of seborrheic keratosis lesions could be achieved but lesions did persist albeit with reduced size. Burkhart et al. further admitted that the selection of patients who were very frustrated with the condition and desired any assistance with their malady may have partially biased the study responses; i.e. even the smallest treatment success was rated very positive. This highlights the strong-felt need of a topical treatment for seborrheic keratosis.

US 2010/0061948 A1 discloses the treatment of skin discolorations in general using skin-whitening compositions comprising artemisinin. Artemisinin (also called Qinghaosu in traditional Chinese medicine) is a sesquiterpene lactone with a peroxide group, which has hitherto been examined and used mainly as a systematically active antimalarial drug. Artemisinin is very hard to dissolve in water; however, more water-soluble derivatives of artemisinin, such as dihydroartemisinin or artesunate have been developed. According to US 2010/0061948 A1, artemisinin allegedly suppressed melanin synthesis and tyrosinase activity to inhibit pigmentation of melasma and freckles. However, the etiopathogenesis of melasma and freckles differs from that of seborrheic keratosis. For example, unlike seborrheic keratosis lesions, freckles (also called lentigo solaris) and melasma are disorders of melanocytes and promoted by sun-light; melasma are further often triggered by drugs such as contraceptive hormones. US 2010/0061948 A1 remains silent on seborrheic keratosis; and the mere suppression of pigmentation alone would not solve the hyperkeratosis, the causation of the lesions, which often leads to clothes, jewelry or razor blades getting caught on seborrheic keratosis lesions, in particular the exophytic ones.

Another skin-whitening composition is described in US 2013/0259815 A1. The application discloses methods of lightening skin by applying certain aromatic compounds to the skin, or botanical extracts containing such compounds, e.g. Acronychia acidula extracts. Various skin conditions in need of lightening (or whitening, brightening, evening of skin tone, reduction in sallowness) are described; mainly hyperpigmented marks and/or lesions including, but not limited to, pigmented spots, melanin spots, age spots, sun spots, senile lentigos, freckles, lentigos simplex, pigmented solar keratosis, seborrheic keratosis, melasma, acne marks, post-inflammatory hyperpigmentation, lentigines, ephelides, combinations of two or more thereof and the like. However, US 2013/0259815 A1 is silent on *Artemisia Annua* extracts and/or artemisinin or derivatives thereof.

U.S. Pat. No. 8,193,376 B2 described formulations, suitable for oral and topical application, for the treatment of infections and topical ailments, such as acne, rosacea, skin discolorations and age spots. The formulations comprise certain derivatives of artemisinin (and other active principles contained in *Artemisia Annua* extracts) with amino acids, peptides, and amino sugars, as well as isomers and salts thereof according to formula:

which possess wide-spectrum antibacterial and antifungal biological activity.

U.S. Pat. No. 8,193,376 B2 further describes artemisinin and its derivatives as having virucidal or virustatic, anti-malarial, anti-cancer and anti-protozoan properties. However, unlike the described acne and rosacea seborrheic keratosis does not involve any bacterial, viral or parasitic infection; and it further does not involve a cancerous degeneration of cell. Thus, seborrheic keratosis would not benefit from any of the properties of artemisinin (or its derivatives) disclosed in U.S. Pat. No. 8,193,376 B2.

Further artemisinin formulations for topical, oral or parenteral application are disclosed by Thornfeldt in e.g. U.S. Pat. No. 4,978,676 A or JPH03-170422. The inventor successfully applied artemisinin and its analogues topically for the treatment of three psoriasis patients; and then further assumed that said compositions should also be effective against hemorrhoids, tubercles, malignant melanoma, keratosis before getting malignant, malignant mole, basal cell cancer, viral tumors (e.g. warts, molluscum contagiosum and orf (Ecthyma contagiosum)); as well as UV-induced skin conditions and tumors (e.g. blistering skin diseases such as xeroderma pigmentosa, pemphigoid or pemphigus; polymorphous light eruption; collagen vascular diseases such as Lupus erythematosus, mixed connective tissue diseases or dermatomyositis; Bowen's disease or squamous cell cancer). However, Thornfeldt does not provide any mechanistic details which would elucidate the relationship between all the above mentioned diseases and/or why all of them would be likely to respond to a treatment with artemisinin or its derivatives. He is further silent on seborrheic keratosis; and none of the disclosed diseases is associated with seborrheic keratosis. (The term "keratosis before getting malignant" in the abstract of JPH03-170422 clearly refers to only those types of keratosis which—unlike seborrheic keratosis—are capable of degenerating to a malignant stadium; e.g. the pre-cancerous and typically UV-induced actinic keratosis).

In EP 1940383 B1 the use of artemisinin or its derivatives in topical formulations is disclosed for the treatment of benign pigmented moles; in particular those of melanocytic origin, such as melanocytic nevi (acquired and congenital), lentigines (sun age spots) or disorders of pigmentation and pigmented macules of the mucous membranes. However, EP 1940383 B1 does not mention seborrheic keratoses. As indicated earlier, seborrheic keratosis and melanocytic lesions (nevi, lentigines) differ significantly in their etiology and pathogenesis. In contrast to melanocytic lesions, seborrheic keratoses are epithelial and not melanocytic proliferations. The melanin pigment in seborrheic keratoses is housed in keratinocytes and not in melanocytes. Seborrheic keratoses are epidermal proliferations that are typified by acanthosis associated with increased number of keratinocytes and papillomatosis of the epidermis that can trigger an increase in the production of melanin in melanocytes and an increased pigmentation of keratinocytes. Keratinocytes in some seborrheic keratoses have been found to harbor specific mutations that are completely different from those found in melanocytic nevi. Melanocytic lesions (nevi, lentigines) on the other hand are melanocytic proliferations characterized by increased numbers of melanocytes and pigmentation. Typical for nevi is the formation of nests of melanocytes in the epidermis or in the dermis and their hyperpigmentation is caused by a substantial increase in the number of melanocytes. As of current knowledge, seborrheic keratoses usually will not turn malignant, while—albeit rarely—a melanoma may develop in a preexisting melanocytic nevus.

SUMMARY OF THE INVENTION

The invention provides a method for the treatment or prevention of seborrheic keratosis which is characterised in that a compound according to formula (1) as defined in claim 1 is locally administered to a subject in need thereof. In another aspect, the invention provides a method for the treatment or prevention of spread of seborrheic keratosis which comprises the local administration of a pharmaceutical composition comprising one or more compounds according to formula (1) to a subject in need thereof. Advantageous embodiments are provided in the dependent claims.

In particular, the compound of formula (1) may be selected from artemisinin, dihydroartemisinin, artesunate and artemether, in particular from artesunate and artemether. The compound may be incorporated in a pharmaceutical composition, e.g. in the form of a topical formulation, such as a paste, an ointment, a suspension, a lotion, a solution, a gel, a spray, a plaster and a cream. The content of the compound in the composition may be in the range from approximately 0.01% to approximately 40% by weight. Optionally, the composition may comprise a combination of two or more compounds of formula (1).

Local administration to the subject may be conducted by locally administering the compound, or the composition comprising the compound, to the skin, in particular to an area of the skin which was or is affected with seborrheic keratosis.

In one specific embodiment of the invention, the subject is further treated by peeling the subject's skin in the area affected with seborrheic keratosis. The peeling may be performed after the administration of a peeling agent, such as an enzyme or a chemical peeling agent.

Moreover, the subject may be co-treated with a further therapeutic agent which is not a compound as defined in any one of claims 1 to 3. The further therapeutic agent may be, for example, a substance for promoting skin healing or an anti-inflammatory substance selected from steroidal or non-steroidal anti-inflammatory drugs. Such agent may optionally be incorporated within the composition comprising the compound(s) of formula (1).

DEFINITIONS

The terms "comprise" or "comprising" with reference to any feature mean that the respective feature must be present, but without excluding the presence of other features.

"A" or an does not exclude a plurality.

"Essentially", "about", "approximately", "substantially" and the like in connection with an attribute or value include the exact attribute or the precise value, as well as any attribute or value typically considered to fall within a normal range or variability accepted in the technical field concerned. For example, "substantially free of water" means that no water is deliberately included in a formulation, but does not exclude the presence of residual moisture.

Percent values are weight-percentages unless indicated otherwise.

The terms active agent, therapeutic agent, active pharmaceutical ingredient (API), active principle, drug, bioactive agent are used synonymously and refer to a compound or combination of compounds which are pharmaceutically active against an undesired condition.

As used herein, the term "seborrheic keratosis" typically refers to the condition as such, while the term "seborrheic keratoses" refers to the visible lesions on the skin of a subject afflicted with the condition.

The term "treatment", as used herein, includes a therapeutic intervention capable of effecting a cure of a disease, condition or symptom; but also an improvement, amelioration, control, control of progression, prevention of progression, prevention of reoccurrence, and the like. The term "prevention" is meant to include the prevention of a disease, condition or symptom, as well as the prevention of further growth and spread and of a reoccurrence or progression after an initial improvement.

As used herein, the term "ointment" refers to a substantially water-free topical formulation comprising an anhydrous, single-phase ointment base and typically an active agent. The term "ointment base" refers to an ointment formulation free of active ingredients.

The terms "patient" and "subject" are used synonymously herein. Typically, the terms refer to humans. However, the invention is not limited to humans only and may be employed in animals if required.

"Combination therapy" or "co-treatment" means that a patient receives two or more treatments concurrently. For example, two different medications are administered to the subject on the same day, using the same or a different route of administration or dosing regimen. The expressions include the treatment with a single pharmaceutical composition comprising two or more active ingredients, in particular active ingredients from different classes.

"Concurrent" or "concurrently" with respect to the components of a combination therapy means that, regardless of any specific administration regimen, the therapy of a patient with a first component of the combination therapy is ongoing while a second component is used.

Any reference signs in the claims should not be construed as a limitation to the embodiments represented in any of the drawings.

A single unit may fulfill the functions of several features recited in the claims.

DETAILED DESCRIPTION OF THE INVENTION

The object of the present invention is to provide an effective treatment or prevention of seborrheic keratosis. This object is attained be the method as defined in claim 1.

In particular, the invention provides a method of treating or preventing seborrheic keratosis which is characterised by the local administration of a compound according to formula (1) to a subject in need thereof:

(1)

wherein:

X represents CO, CHOZ or CHNRZ;

Z is selected from hydrogen; straight-chain and branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; ($C_7$-$C_{24}$) aralkyl; m- and p-$CH_2$ ($C_6H_4$)COOM; $COR^3$; $CSR^3$; $C(NR^6)R^3$; $SOR^4$; $SO_2R^3R^3N$; $SO_2OM$; $SO_2NR^7R^8$; $SO_2O$-artemisinyl; $SO_2NH$-artemisinyl; $POR^4R^5$; $PSR^4R^5$; and $SO_2R^3$;

$R^3$ is selected from straight-chain or branched ($C_1$-$C_6$) alkyl; straight-chain or branched ($C_1$-$C_6$) alkoxy; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; ($C_6$-$C_{10}$) aryloxy; ($C_7$-$C_{24}$) aralkyl; —$(CH_2)_n$—COOM, with n being an integer of from 1 to 6; and 10α-di-hydroartemisinyl;

$R^4$ and $R^5$ are independently selected from straight-chain or branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; ($C_7$-$C_{24}$) aralkyl; OM; straight-chain or branched ($C_1$-$C_6$) alkoxy; ($C_6$-$C_{10}$) aryloxy; and $NR^7R^8$;

$R^6$ is selected from straight-chain or branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; and ($C_7$-$C_{24}$) aralkyl;

M represents hydrogen or a pharmaceutically acceptable cation;

$R^7$ and $R^8$ are independently selected from straight-chain or branched ($C_1$-$C_6$) alkyl, or $R^7$ and $R^8$ together form a ($C_4$-$C_6$) alkylene bridge; and R is selected from hydrogen; straight-chain or branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; and ($C_7$-$C_{24}$) aralkyl.

Where different configurations of substituents are chemically feasible, each of them is meant to be encompassed. For instance, the substituent "X=CHNRZ" may be understood as:

It was surprisingly found that seborrheic keratosis lesions may be successfully treated with such compounds when administered locally. The lesions treated according to the invention do not spread, grow, or mature further. Instead, they become smaller and lighter in color and finally turn almost invisible in most cases.

It was also surprisingly observed that, during treatment of already affected skin areas (which may be more prone to develop further lesions) with the compounds of formula (1), the formation of new, or more, seborrheic keratosis lesions on said skin areas is successfully prevented. While the topical use of artemisinin derivatives for the treatment of moles has been known in the art, these effects are entirely unexpected due to the inherent differences in the etiopathogenesis between lesions of keratinocytic origin (i.e. seborrheic keratosis) and pigmented moles of melanocytic origin (i.e. nevus cell nevi, lentigos or pigmented moles of the mucous membranes).

As used herein, a subject in need of the treatment of the invention is a subject or patient having seborrheic keratosis or having a particular risk of developing seborrheic keratosis. Alternatively, the subject was previously affected by seborrheic keratosis and is at risk of reoccurrence of seborrheic keratosis. Optionally, the method of the invention further includes a step of identifying a subject being affected by seborrheic keratosis and/or being at risk of reoccurrence of seborrheic keratosis, which step is conducted prior to the local administration of the compound of formula (1) to that subject.

In one of the preferred embodiments, the compound of formula (1) is selected from artemisinin, dihydroartemisinin, carboxyl group containing compounds such as artesunate, artemether, arteether, propyl carbonate of dihydroartemisinin, artemisone and artelinic acid; and/or from compounds wherein X is CHOZ and Z is selected from m- and p-CH2 (C6H4) COOM and COR3, and R3 represents —(CH2)n-COOM. With the compounds where X is CHOZ, the configuration at the C atom of the CHOZ group (i.e., the $C_{10}$ atom of the sesquiterpene backbone) may be (R) or (S). The compound may also be used in the form of a $C_{10}$-epimer mixture, wherein the ratio of the two epimers may be caused by the reduction of artemisinin and/or by the exchange of the $C_{10}$-hydroxyl group for a different hydroxyl derived from water or for one of the nucleophiles used in the synthesis.

In a further preferred embodiment, the compound of formula (1) is selected from the group consisting of artemisinin, dihydroartemisinin, artesunate and artemether. In particular, artesunate and artemether are preferred compounds for carrying out the invention.

The compounds of formula (1) may be used individually or as a combination of two or more of these compounds in the method of the invention.

As mentioned, the compounds of formula (1) are known. They may be isolated from plants or obtained from commonly known biological fermentation processes. For example, artemisinin (X is CO) may be isolated from the plant *Artemisia Annua*. Dihydroartemisinin (X is CHOH) may be prepared, for example, by the reduction of artemisinin with sodium borohydride in methanol at approximately 0° C. Detailed information on how to obtain the compounds of formula (1) can be found e.g. in EP 1940383 B1 which is incorporated herein.

The invention further provides a method of treating or preventing seborrheic keratosis comprising the local administration of a pharmaceutical composition comprising one or more compounds of formula (1) as described above to a subject in need thereof. In particular, the composition may comprise one or more of the preferred compounds, such as artemisinin, dihydroartemisinin, artesunate and artemether.

The compound or composition may be administered by local administration to an area of the subject's skin which was or is affected with seborrheic keratosis. Local administration to the skin may be conducted manually and optionally with the use of an application aid or device. The skin area which is affected with seborrheic keratosis is the site of a seborrheic keratosis lesion.

According to a preferred embodiment, the compound of formula (1) may be formulated in a formulation (or preparation, or composition) suitable for local application, in particular for topical (cutaneous) application. Such topical formulation may, for example, be a paste, an ointment, a suspension, a lotion, a solution, a gel, a spray, a plaster or a cream, as will be described in further detail below.

The content, or concentration, of the compound of formula (1) in such formulation may be selected from a broad range since artemisinin derivatives have shown to be well tolerated. In one embodiment, the content of the compound is in the range from approximately 0.01% to approximately 40% by weight, based on the weight of the formulation. Optionally, the content is in the range from approximately 0.1% to approximately 20% by weight, or from approximately 0.1% to approximately 10% by weight. In a further embodiment, the content is in the range from approximately 0.5% to approximately 3% by weight.

The precise therapeutically or prophylactically required quantity of active agent depends on the active agent itself, the selected base, the galenic form (such as ointment, suspension, pastes, plaster, cream, gel, solution, lotion) and on the additives. The suitable concentrations for the treatment or prevention of seborrheic keratosis may also vary from the above listed ranges when working with locally active formulations other than topical ones. Nonetheless, the provided ranges provide a first indication; other suitable concentrations that yield a good balance between effectiveness, tolerability and stability may then be determined by one skilled in the art by simple effectiveness tests, and thus do not fall outside the scope of the present invention.

As mentioned, the composition may comprise more than one compound of formula (1), i.e. a combination of two or more of such compounds, for example of two or more compounds selected from artemisinin, dihydroartemisinin, artesunate and artemether. The content of the combination of the compounds in the formulation may be in the range from approximately 0.01% to approximately 40% by weight, or from approximately 0.1% to approximately 20% by weight, or from approximately 0.1% to approximately 10% by weight, or from approximately 0.5% to approximately 3% by weight, respectively.

The duration of the treatment of seborrheic keratosis depends on the size, manifestation (structure), pigmentation and the "age" of the lesions. Preferably, the treatments are carried out daily (e.g. once or twice daily) or cyclic (e.g. 2 to 3 times per week and twice daily application). Initial reactions are often visible after the first few days of treatment already. However, it may take a few weeks before there is a clear improvement, fading and/or finally disappearance of the lesion. This period may be longer in the case of older patients, even up to several months, since the renewal of the epidermis takes longer with increasing age.

It may be desirable for the method according to the invention that the active substance penetrates into the skin to different depths depending on the therapeutic approach; e.g. for the treatment of seborrheic keratosis, the active agent may preferably penetrate the epidermis and into the upper layers of the dermis (underlying the epidermis), depending on the size and age of the lesion. Various factors may have an impact on the penetration depth.

The penetration may be controlled, for example, by the drug concentration in the formulation, the amount of formulation that is administered to the skin, the dosing frequency, the type of formulation, the selected excipients, and further by manipulation of the site of administration, e.g. by skin needling, stripping or peeling, or by occluding the site.

The formulation type and base may therefore be selected with an eye on the desired skin penetration behavior, but also in consideration of the required product stability. Suitable formulation bases may be selected from the bases commonly used for topical formulations which are inert toward these agents. More lipophilic formulation bases may be preferred for some compounds for stability reasons. For example, a lipophilic formulation such as an ointment may be used for artesunate. Suitable ointment bases include petrolatum, fats, waxes, fatty acid esters, paraffins, oils, silicones and polymers thereof (e.g., polydialkylsiloxanes, silicone elastomers, silicone waxes, silicone emulsifiers). Optionally, the formulation may be substantially free of water. Preferred ointment bases include silicones and polymers thereof; and ointment bases with a lipid content of at least 95%, more preferably at least 99%. Examples of such ointment bases include Excipial® almond oil ointment and Excipial® fat ointment, as commercially available in Germany and Switzerland. In one specific embodiment, the topical formulation is an ointment comprising 10% artesunate in an ointment base with a lipid content of at least 99%; e.g. 10% artesunate in Excipial® fat ointment.

Such ointments, as a further benefit, reduce the loss of moisture from the skin. This occlusion effect leads to warming and acts as a natural penetration enhancer because the "trapped" water causes a slight swelling of the epidermis' top layers. On the other hand, very lipophilic vehicles such as fat or silicone ointments typically have limited appeal to the patient due to their greasy, fatty, sometimes sticky consistency as well as the fact that often such vehicles are not well absorbed by the skin and may thus lead to grease spots in clothing and linen and/or cross-contamination from one subject to another.

Therefore, hydrophilic and/or aqueous based topical formulation bases may be preferred from the user's point of view, such as hydrogels, lotions, sprays or creams. In such type of formulation, the active ingredient may require protection from degradation and/or hydrolysis, e.g., by nano-encapsulation, enclosure in liposomes or complexing with cyclodextrins, such as described in US 2005/1187189 A1.

To increase the stability and shelf life of the product, the composition may be provided in two or more components from which a ready-to-use formulation is reconstituted at the beginning of the treatment. An example for such type of product is the two-compartment, mucoadhesive gel formulation comprising 5% artesunate in a Carbopol® gel which has been proposed for rectal application in severely ill, pediatric malaria-patients (Gaudin et al.; Int. J. Pharm. 353; 2008; p. 1-7). Similar gels may be used for the topical application to seborrheic keratosis lesions according to the invention. The storage of artesunate in dry state together with the Carbopol® powder separately from a liquid carrier for reconstitution increases the shelf life of the product. After reconstitution, the gels should be used within a few days. For routine application in the treatment or prevention of seborrheic keratosis, the gels may also be stabilized by the incorporation of a stabiliser or provided in single dose applicators such as pre-filled double-chamber syringes with a connector for mixing powder and liquid phase, to allow for an easy 'on-demand' preparation of single.

In an alternative embodiment of the method, the composition may be in the form of a cream, i.e. a two-phase system of aqueous and lipophilic fat, or oil, phases. Suitable components of the lipophilic phase of such creams include the same substances as exemplified above for the ointment bases. In addition to water, the aqueous phase may optionally comprise one or more buffering agents (to cause a pH of the aqueous phase well tolerated by the skin), gel forming polymers, such as hydroxypropylmethylcellulose, carboxymethylcellulose, polyvinyl alcohol with cross-linkers (such as borax or multivalent metal cations such as $Mg^{2+}$ or $Ca^{2+}$), stabilizers, vitamins, moisturizers and the like. For emulsification, conventional surface-active substances well tolerated by the skin such as, e.g., fatty acid mono- and diglycerides, PEG-40 hydrogenated castor oil (Cremophor®) or lecithin may be used.

Suitable auxiliary agents which may optionally be added to all topical formulations used in a method according to the invention (ointments, creams, etc.) include among others conventional penetration accelerators (such as dimethylacetamide, dimethylformamide, propylene glycol, fatty alcohols, triethanolamine, dimethylsulfoxide, azones and the like), stabilizers, moisturizers, vitamins and preservatives. Said additives may generally serve to improve effectiveness, stability, durability, consistency and spreadability of the galenic form; and should thus be employed only to the extent and in the amounts required for this purpose.

In a specific embodiment of the method according to the invention, the formulations may be provided in double- or multi-chamber tubes. Various types of these tubes may be suitable. For example, a double-chamber tube wherein one chamber may be filled with a stable pre-concentrate of the compound(s) of formula (1), such as a silicone-based formulation, whereas the other chamber may hold an aqueous base or carrier, such as a liquid, cream, lotion or hydrogel. Upon squeezing the tube, both formulations will be discharged and preferably mixed in the desired ratio at the tip of the tube in order to form a final formulation with the desired concentration of the compound(s) of formula (1) and a more attractive skin feel and/or penetration behavior than the pure silicone-based formulation would have.

Alternatively, the double- or multi-chamber tube may have two (or more) chambers separated by a thin diaphragm. One chamber may again house the storage stable formulation of the compounds of formula (1), e.g. in the form of a pure drug powder, a mixture of the pure drug with other solid excipients such as polymerisation or gelling agents or a drug suspension in a fat or silicone base, while the other holds a second, preferably aqueous, base formulation which is free of the compounds of formula (1), e.g. a cream, lotion or hydrogel. Prior to use the tube is squeezed vigorously without opening the tip, such that the diaphragm is torn and the contents of the two (or more) chambers mixed to form the final formulation. In the latter case, though, the final formulation may not be stable anymore if the drug, e.g. artesunate, is mixed with an aqueous base formulation. As with the above mentioned mucoadhesive gel, the final formulation in the "diaphragm-tube" may be further stabilized for routine application, or provided in single-dose-tubes with amounts appropriately sized to be used up within a short period of time.

In another preferred embodiment, the method for treating or preventing seborrheic keratosis according to the invention is conducted with subjects that are further treated by needling or peeling the subject's skin in an area affected with seborrheic keratosis.

The needling of the skin may involve rotatable microneedle devices (e. g. Dermaroller®) which are rolled over the skin, or microneedle patches which are typically pressed onto the skin (either manually or employing a dedicated applicator) such that the microneedles pierce through the upper skin layers in order to enhance the skin penetration and thus accelerate the treatment and/or prevention and improve its effectiveness. Optionally, the microneedles may be dissolvable. Further optionally the microneedles may be loaded with an active pharmaceutical ingredient (API).

The peeling of the subject's skin may simply consist of the mechanical removal of the skin, or it may involve the pretreatment of the affected skin with one or more peeling agents.

The primarily mechanical removal of the upper skin layer (stratum corneum) may involve the use of abrasive bodies such as salt crystals, sugar crystals, sand or plastic micro-beads. Optionally, peeling devices such as a laser peeling device or a micro-dermabrasion device may also be used. Moreover, sticky materials such as tapes or waxes may be used for skin removal.

Mechanical peels are peelings where skin cells are removed by a physical rather than a chemical action; e.g. by abrasion. In its most simple form, the subject uses his/her fingernails to digitally scrape off loose, shedding or flaky layers of skin. Alternatively, abrasive materials such as sponges, mittens, compacts, pumices or stones with a rough surface may be used. A further easy and long-known method of mechanical peels is the use of abrasive bodies such as salt crystals, sugar crystals, sands such as quartz sand or healing earth, micro-beads from waxes (e.g. jojoba beads), plastic micro-beads (e.g. polyethylene, polypropylene, polyurethane) or ground natural materials such as coffee, wood dust, husks and/or stones of olives, apricots, peaches, or walnuts. These abrasive bodies may be applied either as such (e.g. dry powder sprinkled on wet skin and rubbed gently) or suspended in a formulation (e.g. micro-beads in a gel base).

Device-associated peels mainly comprise microdermabrasion and laser-abrasion. Microdermabrasion is a technique where minute mineral crystals such as aluminum oxide, quartz or the like are blown through a nozzle onto the skin. Simultaneously, the crystals as well as any removed skin are sucked from the skin by vacuum. Laser-peeling, e.g. with erbium-, $CO_2$-laser, is typically done under local anesthesia and uses thermal energy to remove the top layers of the skin.

Optionally, the peeling of the subject's skin is performed after the administration of a peeling agent. Such peeling agent may be selected from enzymes or from chemical peeling agents, or any combinations thereof.

Enzymatic peelings may be performed using proteases (protein cleaving enzymes) such as plant-derived papain or bromelain. The effect is moderate, typically very well tolerated and the microcirculation of the skin is not affected.

In contrast, chemical peelings often increase the skin's microcirculation and the peeling effect typically is far more pronounced than with enzymatic peelings, depending on the selected chemical agent. Examples of chemical peeling agents include urea, retinoic acids, alpha-hydroxy acids (also called AHA or fruit acids), beta-hydroxy acids, trichloroacetic acid, succinic acid, ascorbic acid and phenolic compounds, or any combinations thereof. Known retinoic acids include the all-trans-retinoic acid tretinoin, the 9-cis-retinoic acid alitretinoin and the 13-cis-retinoic acid isotretinoin. These substances have been banned from cosmetic applications and are only available in prescription formulations in most countries. Successors of these retinoic acids were alpha-hydroxy acids, mainly the commonly used citric acid, glycolic acid and lactic acid. Further alpha-hydroxy acids include tartaric acid, malic acid, mandelic acid, fumaric acid and oxalic acid. Similar to the proteases, alpha-hydroxy acids help dissolve the bonds of protein that hold skin cells together, thereby making it easier to remove them and thus exfoliating the skin. A similar effect is also achieved by beta-hydroxy acids such as salicylic acid and 2-hydroxy-5-octanoyl-salicylic acid. These phenolic substances have the additional beneficial effect of acting anti-inflammatory and anti-microbial, and penetrating deeper into the skin due to their increased lipophilicity. Another phenolic compound used for chemical peelings is resorcinol; it is mostly used in combinations such as Jessner's peel solution: salicylic acid, lactic acid, and resorcinol in an ethanol base. Chemical peelings with trichloroacetic acid are very effective and may even be painful, which is why they are usually done under local anesthesia. The skin-shedding effect lasts between several months to several years.

In another embodiment, the method of the invention is carried out with a subject that is co-treated with a further therapeutic agent which is not a compound of formula (1). In particular, the co-treatment may also comprise the local administration of the further therapeutic agent to an area of the subject's skin which was or is affected with seborrheic keratosis.

The co-treatment may involve the administration of the further therapeutic agent incorporated in a separate composition or formulation. Alternatively, the further therapeutic agent may be incorporated within the composition that also comprises the compound of formula (1) as defined herein; i.e. both compounds being incorporated in the same composition or formulation. If the co-treatment involves the use of two different formulations, these may be administered simultaneously or at different times within the same treatment cycle. The two different compositions or formulations may optionally be combined within a kit.

The further therapeutic agent may optionally be a substance for promoting skin healing or an anti-inflammatory substance selected from steroidal or non-steroidal anti-inflammatory drugs such as corticosteroids, salicylic acid derivatives, phenylacetic acid derivatives, indole acetic acid derivatives, arylpropionic acid derivatives, aminobenzoic acid derivatives and benzothiazines.

Examples of suitable corticosteroids include hydrocortisone, prednisolone, clobetasone, fluocortine, desonide, triamcinolone, triamcinolone acetonide, dexamethasone, betamethasone, budesonide, mometasone, methylprednisolone aceponate, beclometasone, hydrocortisone aceponate, fluticasone, prednicarbate, clobetasol propionate. Examples of potentially useful non-steroidal anti-inflammatory drugs include salicylic acid, acetylsalicylic acid, diclofenac, indomethacin, ibuprofen, flurbiprofen, naproxen, ketoprofen, tiaprofenic acid, flufenamic acid, mefenamic acid, piroxicam, tenoxicam, and meloxicam. Examples of substances for promoting skin healing include panthenol (pro-vitamin B5), vitamin B3, ascorbic acid, vitamin E, coenzyme Q10, healing earth, zinc and rosemary oil.

Optionally, the method of the invention may also involve occlusion of the affected skin area of the administration of the compound or composition by means of a plaster. Alternatively, the plaster itself may be loaded with a composition comprising a compound of formula (1), e.g. in the form of a paste, ointment, suspension, solution, gel, spray, lotion or cream. The plaster may comprise a material which holds, takes up or absorbs the drug formulation. Alternatively, the active agent may be directly suspended or dissolved in an inert adhesive of the plaster. In this manner, the active agents may be in direct contact with the location to be treated over a longer period; at the same time providing an easy-and-fast-to-use formulation with reproducible doses to the patient, leading to greater user comfort and better compliance. Furthermore, the plaster may provide the extra benefit of covering and protecting those lesions elevated above the skin level, which may else get easily caught in clothing, jewelry and/or razors. This helps to reduce the risk for infections.

Further forms of application suitable for the method according to the invention include pastes, solutions, suspensions, lotions, gels and sprays. The semisolid or liquid formulations of the cited active agents may also be present in the form of a stick (e.g. like a felt tip for precise dosage) or a roller (with active agent in a suitable liquid or semisolid base, e.g. as a solution, suspension, lotion, gel or cream).

Further examples of local forms of application that may be used in a method according to the invention are applicators that increase the penetration of the active compound into the skin by means of ultrasound, electric fields or, as mentioned above, microneedles. Known applicators that use ultrasound and may be used according to the invention are disclosed e.g. in U.S. Pat. No. 6,908,448 B2 which is hereby incorporated by reference. Applicators that use electric fields for the application of the active agents (principle of iontophoresis) are also known to the skilled person. For known applicators with microneedles for the local application according to the invention of active agents to the skin, reference may be made by way of example to US 2005/065463 A1 which is likewise incorporated by reference herein. US 2005/065463 A1 describes a microneedle patch with drug-loaded needles, the needles being made of a material that is capable of disintegration and dispersion into the skin. Further examples of suitable microneedle devices include drug-free microneedle patches; or rotatable devices such as the Dermaroller®.

In summary, a low-risk, non-invasive method for the treatment or prevention of seborrheic keratosis with artemisinin and derivatives thereof has been provided. The method is painless and simple and healthy tissue is not damaged. Further, no allergic skin reactions were observed with the provided topical treatment. In view of the results obtained so far, it may be assumed that the provided method for the treatment or prevention of seborrheic keratosis with artemisinin and derivatives is very effective and provides a more cost-effective and lower risk means compared to traditional, often invasive treatment methods. The method thus represents an enormous progress and is of great significance not only medically but also socioeconomically.

While some specific embodiments have been described in detail and have been shown in figures, it is to be understood that the invention is not limited to the specific embodiments in the description or in the figures alone. Other advantageous combinations of all disclosed features are feasible and fall under the scope of this invention.

EXAMPLE 1

Topical Artesunate for the Treatment of Seborrheic Keratosis

Figure 1:
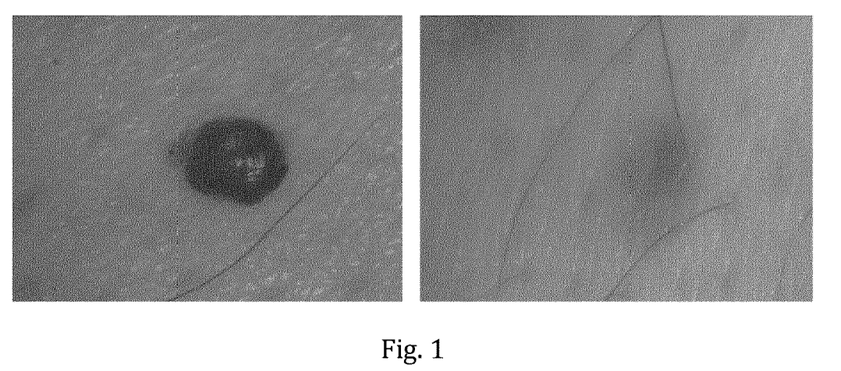
FIG. 1 shows a seborrheic keratosis lesion located at a subjects trunk on day 0 (left) and on day 42, i.e. 6 weeks after treatment started (right).
Figure 2:
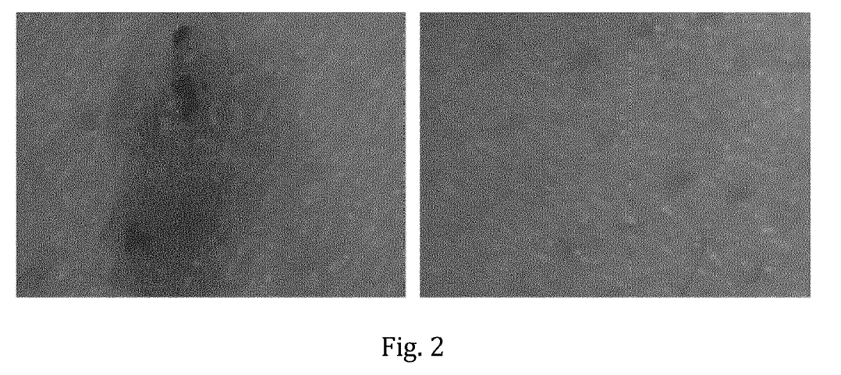
FIG. 2 shows a seborrheic keratosis lesion located on a subject's trunk on day 0 (left) and on day 42, i.e. 6 weeks after treatment started (right).

In a preliminary in vivo study, a formulation comprising 10% artesunate in Excipial® fat ointment (three grams of artesunate stirred homogenously with 27 g of Excipial® fat ointment) was applied topically once daily to five seborrheic keratosis lesions in two patients. Pictures of the lesions on day 0 (baseline) were taken using a Digital 1-CCD video camera, and followed-up 6 weeks after treatment start for patient 1 and 3 months after treatment start for patient 2.

As main outcomes/measures of the study the change in the overall pigmentation and regression of the lesion were measured using a 5-point scale (0-5; 0=no change; 5=disappeared). The effectiveness score was defined as the sum of these 2 ratings (range 0-10) and was determined on day 42 (6 weeks) for 4 lesions and on day 90 for 1 lesion after treatment start. The effectiveness was calculated as percentage change from baseline, setting the highest score of 10=100%. The results are summarized in Table 1 below.

All lesions in both subjects showed clear regression in size and color; being less colored, or pigmented; less elevated above skin level, or have completely disappeared. One lesion increased in size, showed inflammation-like reactions, started to itch and peeled off. The treatment for this lesion was thus shifted from once daily to 2-3 times per week; and after 6 weeks the respective lesions disappeared (100% effectiveness). One large lesion on the face almost disappeared after 3 month of treatment (90% effectiveness) and the other 3 lesion were far less visible (with an effectiveness score of 60 to 90%).

TABLE 1

| Location | Treatment duration [d] | Change Score Pigmentation | Change Score Lesion Regression | Effectiveness (score/%) |
|---|---|---|---|---|
| Face | 42 | 4 | 3 | 7/70% |
| Trunk | 35 | 3 | 3 | 6/60% |
| Trunk | 35 | 4 | 5 | 9/90% |
| Trunk | 28 | 5 | 5 | 10/100% |
| Face | 90 | 5 | 4 | 9/90% |

The invention claimed is:

1. A a method of treating or preventing seborrheic keratosis, wherein the method comprises administering to an area of a subject's skin which was or is affected by seborrheic keratosis a pharmaceutical composition which comprises one or more compounds of formula (1):

wherein:
X represents CO, CHOZ or CHNRZ;
Z is selected from hydrogen; straight-chain and branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; ($C_7$-$C_{24}$) aralkyl; m- and p-$CH_2(C_6H_4)$COOM; $COR^3$; $CSR^3$; $C(NR^6)R^3$; $SOR^4$; $SO_2R^3R^3N$; $SO_2OM$; $SO_2NR^7R^8$; $SO_2$O-artemisinyl; $SO_2NH$-artemisinyl; $POR^4R^5$; $PSR^4R^5$; and $SO_2R^3$;
$R^3$ is selected from straight-chain or branched ($C_1$-$C_6$) alkyl; straight-chain or branched ($C_1$-$C_6$) alkoxy; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; ($C_6$-$C_{10}$), aryloxy; ($C_7$-$C_{24}$) aralkyl; —$(CH_2)_n$—COOM, with n being an integer of from 1 to 6; and 10α-di-hydroartemisinyl;
$R^4$ and $R^5$ are independently selected from straight-chain or branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; ($C_7$-$C_{24}$) aralkyl; OM; straight-chain or branched ($C_1$-$C_6$) alkoxy; ($C_6$-$C_{10}$) aryloxy; and $NR^7R^8$;
$R^6$ is selected from straight-chain or branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; and ($C_7$-$C_{24}$) aralkyl;
M represents hydrogen or a pharmaceutically acceptable cation;
$R^7$ and $R^8$ are independently selected from straight-chain or branched ($C_1$-$C_6$) alkyl, or $R^7$ and $R^8$ together form a ($C_4$-$C_6$) alkylene bridge; and
R is selected from hydrogen; straight-chain or branched ($C_1$-$C_6$) alkyl; straight-chain or branched ($C_2$-$C_6$) alkenyl; straight-chain or branched ($C_2$-$C_6$) alkynyl; ($C_3$-$C_8$) cycloalkyl; ($C_6$-$C_{24}$) aryl; and ($C_7$-$C_{24}$) aralkyl;
in an amount which is efficient for treating or preventing seborrheic keratosis.

2. The method of claim 1, wherein the one or more compounds of formula (1) are selected from artemisinin, dihydroartemisinin, carboxyl group-containing compounds of formula (1), artemether, arteether, propyl carbonate of dihydroartemisinin, artemisone, artelinic acid; and/or wherein X is CHOZ and Z is selected from m- and p-$CH_2(C_6H_4)$ COOM and $COR^3$, and $R^3$ represents —$(CH_2)_n$—COOM.

3. The method of claim 1, wherein the one or more compounds of formula (1) are selected from artemisinin, dihydroartemisinin, artesunate, and artemether.

4. The method of claim 1, wherein the composition is present in the form of a topical formulation selected from a paste, an ointment, a suspension, a lotion, a solution, a gel, a plaster, a spray, a cream.

5. The method of claim 1, wherein the composition comprises from about 0.01% to about 40% by weight of the one or more compounds of formula (1).

6. The method of claim 5, wherein the composition comprises from about 0.1% to about 10% by weight of the one or more compounds of formula (1).

7. The method of claim 5, wherein the composition comprises from about 0.5% to about 3% by weight of the one or more compounds of formula (1).

8. The method of claim 1, wherein the composition comprises at least two compounds of formula (1).

9. The method of claim 8, wherein the composition comprises the at least two compounds of formula (1) in a total concentration of from about 0.01% to about 40% by weight.

10. The method of claim 1, wherein the method further comprises needling or peeling the subject's skin in an area affected with seborrheic keratosis.

11. The method of claim 10, wherein peeling the subject's skin involves using abrasive bodies and/or using a peeling device and/or manual removal of affected skin.

12. The method of claim 11, wherein the abrasive bodies comprise bodies selected from one or more of salt crystals, sugar crystals, sand and plastic micro-beads and/or wherein the peeling device comprises one or both of a laser peeling device and a micro-dermabrasion device.

13. The method of claim 11, wherein peeling of the subject's skin is performed after administration of a peeling agent.

14. The method of claim 13, wherein the peeling agent is selected from one or more of enzymes, urea, retinoic acids, trichloroacetic acid, ascorbic acid, succinic acid, alpha-hydroxy acids, and beta-hydroxy acids.

15. The method of claim 1, wherein the subject is co-treated with an additional therapeutic agent which is not a compound of formula (1), and wherein the co-treatment comprises local administration of the additional therapeutic agent to an area of the subject's skin which was or is affected with seborrheic keratosis.

16. The method of claim 15, wherein the additional therapeutic agent is a substance for promoting skin healing or an anti-inflammatory substance selected from steroidal or non-steroidal anti-inflammatory drugs.

17. The method of claim 16, wherein the additional therapeutic agent is selected from one or more of corticosteroids, salicylic acid derivatives, phenylacetic acid derivatives, indole acetic acid derivatives, arylpropionic acid derivatives, aminobenzoic acid derivatives, and benzothiazines.

18. The method of claim 16, wherein the anti-inflammatory substance is selected from one or more of hydrocortisone, prednisolone, clobetasone, fluocortine, desonide, triamcinolone, triamcinolone acetonide, dexamethasone, betamethasone, budesonide, mometasone, methylprednisolone aceponate, beclometasone, hydrocortisone aceponate, fluticasone, prednicarbate, clobetasol propionate, salicylic acid, acetylsalicylic acid, diclofenac, indomethacin, ibuprofen, flurbiprofen, naproxen, ketoprofen, tiaprofenic acid, flufenamic acid, mefenamic acid, piroxicam, tenoxicam, and meloxicam.

19. The method of claim 1, wherein preventing seborrheic keratosis comprises prevention of further growth and spread of seborrheic keratosis and prevention of a reoccurrence or progression of seborrheic keratosis after an initial improvement.

20. The method of claim 1, wherein the one or more compounds of formula (1) are selected from artesunate and artemether.

* * * * *